US011028415B2

(12) United States Patent
Cucchetti et al.

(10) Patent No.: US 11,028,415 B2
(45) Date of Patent: *Jun. 8, 2021

(54) PROCESS FOR THE PRODUCTION OF LIPIDS FROM BIOMASS DERIVED FROM GUAYULE PLANTS

(71) Applicants: Eni S.P.A., Rome (IT); Versalis S.P.A., San Donato Milanese (IT)

(72) Inventors: Daniela Cucchetti, Cuggiono (IT); Ezio Battistel, Casalino (IT); Chiara Gambaro, Trecate (IT); Alessandra D'Arminio Monforte, Milan (IT)

(73) Assignees: Versalis S.P.A., San Donato Milanese (IT); Eni S.P.A., Rome (IT)

(*) Notice: Subject to any disclaimer, the term of this patent is extended or adjusted under 35 U.S.C. 154(b) by 0 days.

This patent is subject to a terminal disclaimer.

(21) Appl. No.: 16/613,405

(22) PCT Filed: Jun. 26, 2018

(86) PCT No.: PCT/IB2018/054689
§ 371 (c)(1),
(2) Date: Feb. 24, 2020

(87) PCT Pub. No.: WO2019/003097
PCT Pub. Date: Jan. 3, 2019

(65) Prior Publication Data
US 2020/0248214 A1    Aug. 6, 2020

(30) Foreign Application Priority Data

Jun. 27, 2017  (IT) .................. 102017000071514

(51) Int. Cl.
*C12P 7/64*    (2006.01)

(52) U.S. Cl.
CPC ......... *C12P 7/6409* (2013.01); *C12P 2203/00* (2013.01)

(58) Field of Classification Search
CPC ....................................................... C12P 7/64
See application file for complete search history.

(56) References Cited

U.S. PATENT DOCUMENTS

| 5,628,830 | A | 5/1997 | Brink |
| 5,916,780 | A | 6/1999 | Foody et al. |
| 6,090,595 | A | 7/2000 | Foody et al. |
| 10,301,656 | B2 * | 5/2019 | Franzosi ............. C12R 1/645 |
| 2017/0088867 | A1 * | 3/2017 | Miglio .................. C11B 1/02 |

FOREIGN PATENT DOCUMENTS

| EP | 1728844 A1 | 12/2006 |
| WO | WO2010046051 A2 | 4/2010 |
| WO | WO2010069516 A2 | 6/2010 |
| WO | WO2010069583 A1 | 6/2010 |
| WO | WO2012042544 A1 | 4/2012 |
| WO | WO2012052368 A1 | 4/2012 |
| WO | WO2015087254 A1 | 6/2015 |
| WO | WO2015162568 A1 | 10/2015 |
| WO | WO2016062753 A1 | 4/2016 |
| WO | WO2016108185 A1 | 7/2016 |
| WO | WO2017021931 A1 | 2/2017 |
| WO | WO2017046720 A1 | 3/2017 |

OTHER PUBLICATIONS

Plant list entry, also avaiable online, Jun. 2020.*
International Search Report for PCT/IB2018/054689 dated Sep. 18, 2018, 9 pages.
Chundawat s. P. S. et al., "Guayule as a feedstock for lignocellulosic biorefineries using ammonia fiber expansion (AFEX) pretreatment", published in "Industrial Crops and Products" (2012), vol. 37, p. 486-492.
Srinivasan N. "Pretreatment of Guayule Biomass Using Supercritical CO2 based Method for Use as Fermentation Feedstock" (2010).
Srinivasan N. et al., "Pretreatment of guayule biomass using supercritical carbon dioxide-based method", published in "Bioresource Technology" (2010), vol. 101, p. 9785-9791.
Humbrid D. et al., In Technical Report Nrel/Tp-51 00-47764 (May 2011).
J. A. Knight et al., "Chemical Basis of the Sulpho-phospho-vanillin Reaction for Estimating Total Serum Lipids", published in "Clinical Chemistry" (1972), vol. 18, No. 3, p. 199-202.
Schmidt E. In "Handbook of Essential Oil. Science, Technology and Application" (2010), Baser K. H. C. and Buchbauer G. Eds., CRC Press, Boca Raton (USA), Chapter 4, p. 99-117.

* cited by examiner

*Primary Examiner* — Maryam Monshipouri
(74) *Attorney, Agent, or Firm* — Praedcere Law (57) ABSTRACT

A process for the production of lipids from biomass derived from guayule plants comprising: obtaining a hydrolysate comprising 5 carbon atom (C5) sugars from biomass derived from guayule plants, said 5 carbon atom (C5) sugars being present in said hydrolysate in a quantity greater than or equal to 80% by weight, preferably ranging from 85% by weight to 99% by weight, with respect to the total weight of said hydrolysate; feeding said hydrolysate to a fermentation device in the presence of at least one oleaginous yeast to obtain a fermentation broth; at the end of fermentation, subjecting said fermentation broth to separation obtaining an aqueous suspension of oleaginous cellular biomass comprising lipids and an aqueous phase. The lipids thus obtained can be advantageously used in the production of biofuel such as, for example, biodiesel or green diesel that can be used as such, or in mixtures with other fuels, for automotive transport.

7 Claims, 2 Drawing Sheets

FIGURE 1

FIGURE 2

PROCESS FOR THE PRODUCTION OF LIPIDS FROM BIOMASS DERIVED FROM GUAYULE PLANTS

The present invention relates to a process for the production of lipids from biomass derived from guayule plants.

More in particular, the present invention relates to a process for the production of lipids from biomass derived from guayule plants comprising: obtaining a hydrolysate prevalently comprising 5 carbon atom (C5) sugars from biomass derived from guayule plants; feeding said hydrolysate to a fermentation device in the presence of at least one oleaginous yeast to obtain a fermentation broth; at the end of fermentation, subjecting said fermentation broth to separation obtaining an aqueous suspension of oleaginous cellular biomass comprising lipids and an aqueous phase.

The lipids thus obtained can be advantageously used in the production of biofuel such as, for example, biodiesel or green diesel that can be used as such, or in mixtures with other fuels, for automotive transport.

Natural rubber is a hydrocarbon polymer (cis-1,4-polyisoprene) contained in hundreds of plant species in the form of an aqueous emulsion normally indicated by the term latex. The main source of natural rubber is *Hevea brasiliensis*, a tree native to the Amazon, and South America remained the main source of the limited quantities of latex required throughout the whole of the 19th century. Currently, because of parasites and diseases, the American plantations have almost all been abandoned and the production of natural rubber is almost entirely concentrated in South East Asia.

To overcome the drawbacks of production that is constantly exposed to diseases and attacks by parasites, over the 20th century, numerous methods were developed for producing synthetic rubber, culminating with the discovery of Ziegler-Natta catalysts that allow isoprene to be polymerized with very high regio- and stereo-selectivity, obtaining a synthetic cis-1,4-polyisoprene that is almost undistinguishable from the one of plant origin. However, natural rubber has never been completely supplanted because some of its properties, mainly mechanical, are actually a result of its content of small quantities of lipids and proteins associated with it. Hence, in the total rubber production of 2013 (27.5 Mt), 12 Mt (43%) of natural rubber are still included.

But, the production of rubber from *Hevea brasiliensis* implies some problems of a technical and ethical nature. In fact, it is still possible that the same diseases and parasites that destroyed the American plantations also affect the South East Asian ones. Furthermore, the harvesting of the latex requires extensive labor and is only profitable because this labor is paid with extremely low salaries. For these reasons, alternative sources of natural rubber are being investigated. Among these, guayule (*Parthenium argentatum*) is certainly one of the most promising.

Guayule (*Parthenium argentatum*) is a perennial shrub originating in the semidesert regions of the South Western USA (particularly Texas) and Northern Mexico. This plant accumulates natural rubber, mainly constituted by the elastomer cis-1,4 polyisoprene, in the form of latex (a milky dispersion or suspension in water) especially in the bark of the branches and of the stem. The natural rubber content can depend on various environmental, farming and preservation factors and is therefore ranging from 5% to 20% with respect to the total weight of the dry plant.

The extraction of natural rubber from guayule plants, as from other plants belonging to the genera of Asteraceae, Euphorbiaceae, Campanulaceae, Labiatae and Moraceae, such as, for example, *Euphorbia lathyris, Parthenium incanum, Chrysothamnus nauseosus, Pedilanthus macrocarpus, Cryptostegia grandiflora, Asclepias syriaca, Asciepias speciosa, Asciepias subulata, Solidago altissima, Solidago gramnifolia, Solidago rigida, Sonchus arvensis, Silphium* spp., *Cacalia atriplicifolia, Taraxacum koksaghyz, Pycnanthemum incanum, Teucreum canadense, Campanula americana* (indicated in short by the term "guayule type"), represents an important alternative to the extraction of natural rubber from *Hevea brasiliensis*, especially considering the greater resistance of these species to pathogenic agents that attack *Hevea*, the lower import costs of the plant raw material and in virtue of the lower content, in rubber extracted from these plants compared to that derived from *Hevea*, of numerous proteic contaminants responsible for type I latex allergies (or IgE-mediated).

However, the production of natural rubber from guayule is only profitable if all the other fractions that constitute the plant are also exploited: mainly resin (present in comparable quantities to that of rubber) and the lignocellulosic fraction, as well as small amounts of essential oils and waxes. In particular, after the extraction of the rubber and the resin, widely described in scientific and patent literature, the lignocellulosic residue (bagasse), comprising lignin and polysaccharides, must be subjected to the saccharification process which consists of a hydrolysis of polysaccharides [which are thus transformed into 5 carbon atom (C5) sugars and six carbon atom (C6) sugars dissolved in the hydrolysate obtained] and leaves a solid residue containing lignin. The sugars thus obtained can then be used for feeding production processes of organic intermediates by fermentation, while the lignin can be exploited as fuel or in other ways.

For example, Chundawat S. P. S. et al., describe the pretreatment of different biomasses derived from guayule with ammonia fiber expansion (AFEX) in order to obtain sugars to be used for producing ethanol, in the following article: "Guayule as a feedstock for lignocellulosic biorefineries using ammonia fiber expansion (AFEX) pretreatment", published in "*Industrial Crops and Products*" (2012), Vol. 37, pg. 486-492. In said article it is analyzed the capacity to ferment sugars present in the hydrolysate obtained from guayule after the aforementioned treatment, comprising both 6 carbon atom (C6) sugars (prevalently) and five carbon atom (C5) sugars, of an engineered strain of *Saccharomyces cerevisiae*, for the purpose of producing ethanol. Furthermore, in said article it is underlined the fact that the fermentation of xylose is slow and that after 24 hours of fermentation there is still about 60% of xylose not used. Srinivasan N. in the thesis "Pretreatment of Guayule Biomass Using Supercritical $CO_2$-based Method for Use as Fermentation Feedstock" (2010), describes the possibility to use hydrolysates derived from guayule plants, comprising both 6 carbon atom (C6) sugars (prevalently), and 5 carbon atom (C5) sugars, as substrates for producing ethanol through fermentation in the presence of the following strains *Kluyveromyces marxianus, Candida shehatae* or *Saccharomyces cerevisiae*. In particular, in said thesis it is analyzed the possibility to perform simultaneous saccharification and fermentation (SSF) in the presence of *Kluyveromyces marxianus*, for producing ethanol.

Srinivasan N. et al., describe the pretreatment of guayule biomass through treatment with supercritical carbon dioxide ($CO_2$) and its subsequent use, after enzymatic hydrolysis, in fermentation for producing bio-products with added value, in the following article: "Pretreatment of guayule biomass using supercritical carbon dioxide-based method", published in "*Bioresource Technology*" (2010), Vol. 101, pg.

9785-9791. In said article, the possibility is verified of using the hydrolysate obtained from guayule, comprising both 6 carbon atom (C6) sugars (prevalently), and 5 carbon atom (C5) sugars, for growing the fungus *Trichoderma reesei*, through fermentation, analyzing the growth and the production of specific enzymes (proteins) such as, for example, cellulase.

International patent application WO 2016/062753 in the Applicant's name relates to an integrated process for processing and utilizing every part of the guayule plant, comprising the following steps in sequence:
- separating the stem and branches from the leaves of said plant with a mechanical treatment;
- treating the leaves to produce waxes and essential oils, and a fraction containing cellulose, hemicellulose and, to a minor extent, salts, organic compounds and lignin;
- extracting from the stem and branches a liquid phase, so forming a first solid woody residue, indicated as bagasse;
- treating said first solid woody residue to form sugars, cellulose, hemicellulose and lignin.

The aforementioned integrated process is said to be able to further utilize the guayule plant by accompanying the production of latex, rubber, resin and bagasse with the production of fermentable sugars: said utilization is particularly important in the case of biorefineries designed to produce organic intermediates other than ethanol, for example, for producing 1,3-butanediol which can be transformed, after its double catalytic dehydration, into bio-butadiene. However, in the aforementioned international patent application, it is not specifically indicated, or suggested, to use 5 carbon atom (C5) sugars in the fermentation of oleaginous yeasts for producing lipids.

It is therefore to be noted how, in the prior art reported above, no reference is made to the use of hydrolysates obtained from treating biomass derived from guayule plants prevalently comprising 5 carbon atom (C5) sugars in the production of organic compounds other than ethanol and, in particular, in the fermentation of oleaginous yeasts for producing lipids.

In fact, it is known that, while the use of 6 carbon atom (C6) sugars for producing organic compounds (for example, ethanol) does not constitute a problem, the same is not true for 5 carbon atom (C5) sugars. The reason is to be looked for in the fact that 5 carbon atom (C5) sugars are metabolically less efficient than 6 carbon atom (C6) sugars as they follow catabolic pathways which are different in part. 6 carbon atom (C6) sugars such as glucose, are catabolized according to the glycolytic pathway, while 5 carbon atom (C5) sugars, such as xylose, enter the cell metabolism according to the pentose phosphate pathway and are only subsequently joined to the final part of the glycolytic pathway: said difference in the catabolic pathway leads to the consumption of 5 carbon atom (C5) sugars, by many microorganisms with clearly slower kinetics than those observed in the consumption of 6 carbon atom (C6) sugars. There are even microorganisms that are not able to use 5 carbon atom (C5) sugars, which are used in the microbiological industry.

Therefore, in general, mixtures of sugars obtained in many biomass hydrolysis processes comprising both 6 carbon atom (C6) sugars, and 5 carbon atom (C5) sugars, do not constitute a suitable feeding for many fermentations, except for the traditional alcoholic fermentation performed in the presence of strains of *Saccharomyces cerevisiae*, appropriately genetically modified, in order to produce ethanol and that are notoriously rather tolerant in terms of feeding quality.

Therefore, the production of hydrolysates with a prevalent 5 carbon atom (C5) sugar content constitutes a problem, in particular in the case of biorefineries designed to produce organic intermediates other than ethanol, for example, for producing 1,3-butanediol which can be transformed, after its double catalytic dehydration, into bio-butadiene.

The Applicant therefore set out to solve the problem of using hydrolysates with a prevalent 5 carbon atom (C5) sugar content obtained from the treatment of biomass derived from guayule plants, for the purpose of producing organic compounds of interest, in particular lipids.

The Applicant has now found that hydrolysates with a prevalent 5 carbon atom (C5) sugar content obtained from the treatment of biomass derived from guayule plants can be advantageously used in the fermentation of oleaginous yeasts for producing lipids.

The use of said hydrolysates allows the range of products obtainable from the guayule plant to be increased, also placing the production of lipids alongside that of latex, rubber, resin and bagasse. Said lipids can be advantageously used in the production of biofuel such as, for example, biodiesel or green diesel that can be used as such, or in mixtures with other fuels, for automotive transport.

Hence, the subject matter of the present invention is a process for the production of lipids from biomass derived from guayule plants comprising:
- obtaining a hydrolysate comprising 5 carbon atom (C5) sugars from biomass derived from guayule plants, said 5 carbon atom (C5) sugars being present in said hydrolysate in a quantity greater than or equal to 80% by weight, preferably ranging from 85% by weight to 99% by weight, with respect to the total weight of said hydrolysate;
- feeding said hydrolysate to a fermentation device in the presence of at least one oleaginous yeast to obtain a fermentation broth;
- at the end of fermentation, subjecting said fermentation broth to separation obtaining an aqueous suspension of oleaginous cellular biomass comprising lipids and an aqueous phase.

For the purpose of the present description and of the following claims, the definitions of the numeric ranges always include the extremes unless specified otherwise.

For the purpose of the present description and of the following claims, the term "comprising" also includes the terms "which essentially consists of" or "which consists of".

For the purpose of the present description and of the following claims, the term "guayule plant" generally means both the *Parthenium argentatum* species and guayule type plants of the species listed above.

For the purpose of the present description and of the following claims, the term "5 carbon atom (C5) sugar" means a pentose sugar, or more simply a pentose, which is a monosaccharide carbohydrate comprising five carbon atoms having the chemical formula $C_5H_{10}O_5$. Likewise, for the purpose of the present description and of the following claims, the term "6 carbon atom (C6) sugar" means a hexose sugar, or more simply a hexose, which is a monosaccharide carbohydrate comprising six carbon atoms having the chemical formula $C_6H_{12}O_6$.

For the purpose of the present description and of the following claims, the term "biomass derived from guayule plants" means any form (for example, the whole plant, parts of the plant, including roots, branches and/or stalks, leaves, any bark, fragments of plant obtained by chopping, grinding etc., briquettes and pellets obtained by compacting plant fragments) wherein the guayule plant is used for the purpose of obtaining, by means of chemical and/or physical methods, latex, rubber, resin, bagasse, sugars and other components present in the plant itself.

For the purpose of the present description and of following claims, the term "bagasse" means the residual portion of plant material deriving from extraction processes to which the guayule plants can be subjected. The bagasse may also include small quantities of non-plant material (for example, soil, sand, etc.) typically associated with the roots of the plants and deriving from the farm land.

For the purpose of the present description and of the following claims, the term "miscella" means a solution, a suspension or an emulsion constituted by latex, rubber and/or resin, water and/or organic solvents, in which the extraction process is performed, obtained after separation of the bagasse.

In accordance with a preferred embodiment of the present invention, said hydrolysate comprising 5 carbon atom (C5) sugars from biomass derived from guayule plants comes from the hydrolysis of the hemicellulose contained in the guayule plants.

In accordance with a further preferred embodiment of the present invention, said hydrolysate comprising 5 carbon atom (C5) sugars from biomass derived from guayule plants comes from the hydrolysis of the hemicellulose contained in the bagasse derived from the extraction processes to which said guayule plants are subjected.

Extraction processes to which guayule plants can be subjected in order to obtain bagasse are known in the state of the art. For the purpose of the present invention, said bagasse can preferably be obtained through the process described in international patent application WO 2016/062753 in the name of the Applicant, reported below.

For the purpose of the present invention, said hydrolysis can be performed by subjecting the biomass derived from guayule plants or the bagasse to any one of the methods known in the art. Non-limiting examples of said methods are:
- heat treatment known as "steam explosion", followed by enzymatic hydrolysis as described, for example, in international patent application WO 2012/042544;
- treatment in the presence of diluted acids, for example diluted sulfuric acid, followed by enzymatic hydrolysis, as described, for example, by Humbrid D. et al., in "Technical Report Nrel/Tp-5100-47764 (May 2011);
- treatment in the presence of organic acids, for example, 2-naphthalenesulfonic acid, followed by enzymatic hydrolysis, as described, for example, in international patent application WO 2010/046051;
- treatment in the presence of an aqueous solution of at least one organic acid having from 1 to 6 carbon atoms, preferably from 1 to 3 carbon atoms, more preferably methanesulfonic acid ($CH_3-SO_3H$), the pH of said aqueous solution being ranging from 0.6 to 1.6, preferably ranging from 0.9 to 1.3, as described, for example, in international patent application WO 2015/087254 in the name of the Applicant;
- treatment in the presence of at least one organic acid selected, for example, from phosphonic acids or alkylphosphonic acids such as, for example, etidronic acid, methane phosphoric acid, as described, for example, in international patent application WO 2016/062753 in the name of the Applicant, reported above.

Preferably, for the purpose of the present invention, said hydrolysis can be performed as described in the aforementioned international patent application WO 2015/087254 in the name of the Applicant or in the aforementioned international patent application WO 2016/062753 in the name of the Applicant.

From the hydrolysis of the biomass derived from guayule plants or of the bagasse performed with one of the aforementioned methods, a mixture is obtained comprising a solid phase (i.e. solid residue) and an aqueous phase (i.e. hydrolysate). Said mixture is subjected to filtration or centrifugation for the purpose of obtaining a solid phase (i.e. solid residue) comprising lignin and cellulose and an aqueous phase i.e. hydrolysate comprising 5 carbon atom (C5) sugars.

Said solid phase (i.e. solid residue) comprising lignin and cellulose can be used in an enzymatic hydrolysis process, for the purpose of hydrolyzing the cellulose to 6 carbon atom (C6) sugars, in particular glucose. The enzymatic hydrolysis process can be performed according to techniques known in the state of the art as described, for example, in American patents U.S. Pat. Nos. 5,628,830, 5,916,780 and 6,090,595, using commercial enzymes such as, for example, Celluclast 1.5L (Novozymes), Econase CE (Rohm Enzymes), Spezyme (Genecor), Novozym 188 (Novozymes), used individually or mixed together. From the enzymatic hydrolysis of said solid phase a further solid phase comprising lignin and a further aqueous phase comprising 6 carbon atom (C6) sugars are obtained, in particular glucose that derives from the hydrolysis of cellulose. Said further solid phase and said further liquid phase can be separated through techniques known in the state of the art such as, for example, filtration, centrifugation. Preferably, said phases are separated by filtration. The 6 carbon atom (C6) sugars, in particular glucose, can be subsequently used in fermentation processes for producing organic intermediates or ethanol, while lignin can be exploited as fuel.

The quantities of sugars obtained after hydrolysis can be determined through techniques that are known in the art such as, for example, high performance liquid chromatography (HPLC), or ion exchange chromatography.

In accordance with a preferred embodiment of the present invention, said fermentation can be performed at a temperature ranging from 20° C. to 40° C., preferably ranging from 25° C. to 35° C.

In accordance with a preferred embodiment of the present invention, said fermentation can be performed for a time ranging from 70 hours to 140 hours, preferably ranging from 95 hours to 130 hours.

In accordance with a preferred embodiment of the present invention, said fermentation can be performed at pH ranging from 4.5 to 7, preferably ranging from 5 to 6.7. For the purpose of maintaining the pH in the desired ranges, to the culture medium used for fermentation, it can be added an aqueous solution of at least one inorganic base such as, for example, sodium hydroxide, potassium hydroxide, magnesium hydroxide, or mixtures thereof, preferably potassium hydroxide; or an aqueous solution of at least one inorganic acid such as, for example, phosphoric acid, sulfuric acid, 2-(N-morpholino)ethanesulfonic acid (MES), hydrochloric acid, or mixtures thereof; in such a quantity so as to obtain the desired pH. Preferably, an aqueous solution of 2-(N-morpholino)ethanesulfonic acid (MES) can be added.

In accordance with a preferred embodiment of the present invention, said oleaginous yeast can be selected from: *Rhodosporidium azoricum*, *Trichosporon pullulans*, *Trichosporon oleaginous*, *Trichosporon cacaoliposimilis*, *Cryptococcus curvatus*, *Rhodotorula gracilis*, *Rhodotorula graminis*, *Lypomices starkeyi*, *Lypomices lipofer*, *Trigonopsis variabi-*

*lis, Candida kefyr, Candida curvata, Candida lipolytica, Torulopsis* sp., *Pichia stipitis*.

In accordance with a particularly preferred embodiment of the present invention, said oleaginous yeast can be selected from: *Rhodosporidium azoricum* DSM 294895 (mutant described in patent application WO 2016/108185), *Trichosporon pullulans* NRRL Y-1522 (commercially available strain), *Trichosporon oleaginous* ATCC 20509 (commercially available strain).

It is to be noted that the oleaginous yeasts used for the purpose of the present invention have demonstrated excellent tolerance to the salts that are generally present in the hydrolysate comprising 5 carbon atom (C5) sugars from biomass derived from guayule plants; in fact, said oleaginous yeasts are able to produce lipids in the presence of conductivity ranging from 0.001 mS/cm to 40 mS/cm.

In accordance with a preferred embodiment of the present invention, said fermentation is a batch fermentation, or a fed-batch fermentation, or a continuous culture fermentation, preferably a batch fermentation or a fed-batch fermentation. In the case of continuous culture fermentation, there can be recirculation of the biomass derived from guayule plants.

For the purpose of the present invention, said fermentation can be performed in a reaction device with internal circulation of the "air-lift" type described, for example, in international patent application WO 2017/046720, or in a "CSTR" (continuous stirred tank reactor).

Preferably, said oleaginous yeast, before being used in said fermentation, can be grown in a culture medium comprising xylose, cellobiose, glucose, or a mixture thereof, at a concentration preferably ranging from 1% by weight to 3% by weight with respect to the total weight of said culture medium.

Said fermentation can be advantageously performed in fermentation devices known in the state of the art, in the presence of culture media comprising various nutrients such as, for example, nitrogen, potassium phosphate, magnesium, salts, vitamins.

In said fermentation device, the fermentation is performed in the presence of culture media comprising, as well as the hydrolysate comprising 5 carbon atom (C5) sugars from biomass derived from guayule plants, various nutrients such as, for example, nitrogen, potassium phosphate, magnesium, salts, vitamins, microelements, normally used in the culture media.

At the end of fermentation, for the purpose of deactivating the lipolytic enzymes (e.g., lipase) the fermentation broth obtained can be subjected to heat treatment, preferably in the presence of sulfuric acid. Said heat treatment can be performed at a temperature ranging from 70° C. to 120° C., preferably ranging from 75° C. to 110° C., for a time ranging from 5 minutes to 8 hours, preferably ranging from 2 hours to 4 hours. In the case of heat treatment in the presence of sulfuric acid, the pH of the aqueous suspension of the resulting oleaginous cellular biomass comprising lipids can be ranging from 1.5 to 6.0, preferably ranging from 2.0 to 4.5; more details on said heat treatment in the presence of sulfuric acid can be found, for example, in international patent application WO 2017/021931.

At the end of fermentation, the separation to which said fermentation broth is subjected for the purpose of recovering said aqueous suspension of oleaginous cellular biomass comprising lipids and said aqueous phase (said aqueous phase optionally comprising suspended solids, for example, cells of the oleaginous microorganism used in fermentation, or particulate deriving from the deterioration of the equipment used in the process, or from the precipitation of salts), can be performed through methods known in the state of the art such as, for example, filtration, filter-pressing, microfiltration or ultrafiltration, centrifugation.

For the purpose of further concentrating the aqueous suspension of oleaginous cellular biomass comprising lipids obtained after separation, said aqueous suspension of oleaginous cellular biomass, before being subjected to lipid recovery (i.e. to cell lysis, extraction with solvent and evaporation of the solvent), can be subjected to centrifugation. Said centrifugation can be performed for a time ranging from 5 minutes to 30 minutes, preferably ranging from 15 minutes to 25 minutes, at a rotation speed ranging from 3000 rpm to 9000 rpm, preferably ranging from 3500 rpm to 8000 rpm.

The concentration of oleaginous cellular biomass can be measured in grams per liter of fermentation broth, determining the dry weight of the oleaginous yeast cells of a sample of fermentation broth of a known volume taken at predefined intervals and at the end of fermentation. In particular, the term "dry weight" of oleaginous cellular biomass means the weight of the cells contained in a known volume of fermentation broth, determined by weighing the aforementioned cells after removing all the water content through filtration on Whatman filters GF/F (0.7 μm) and subsequent heat treatment in a ventilated oven at 105° C. until constant weight (about 24 hours).

For the purpose of recovering the lipids, said aqueous suspension of oleaginous cellular biomass comprising lipids, can be subjected to cell lysis that can be performed through various methods. Non-limiting examples of said methods are:

heat treatment, which can be performed using pressurized autoclaves (for example, Brignole autoclave Mod. AU-2, or agitated Parr reactor Mod. PA 4575), at a pressure ranging from 2 bar to 6.5 bar, preferably ranging from 3 bar to 5.5 bar, at a temperature ranging from 100° C. to 160° C., preferably ranging from 1100° C. to 150° C., for a time ranging from 1 hour to 8 hours, preferably ranging from 1.5 hours to 4 hours, under stirring ranging from 100 rpm to 800 rpm, preferably ranging from 400 rpm to 600 rpm, as described, for example, in international patent application WO 2012/052368;

mechanical treatment, which can be performed using high pressure homogenizers for example, homogenizer Mod. NS3006L made by Gea NiroSoavi), at a pressure ranging from 800 bar to 2000 bar, preferably ranging from 1000 bar to 1600 bar, at a temperature ranging from 10° C. to 100° C., preferably ranging from 20° C. to 80° C., at a flow rate of the aqueous suspension of oleaginous cellular biomass ranging from 5 l/h to 50 l/h, preferably ranging from 7 l/h to 40 l/h;

treatment with microwaves, which can be performed using microwave equipment (for example, microwave equipment Mod. MycroSYNTH made by Milestone), at a temperature ranging from 45° C. to 150° C., preferably ranging from 50° C. to 100° C., for a time ranging from 10 minutes to 2 hours, preferably ranging from 15 minutes to 1 hour.

At the end of said cell lysis, the lipids can be recovered from the exhausted aqueous suspension of cellular biomass comprising lipids obtained, through extraction using, for example, a reflux extractor.

Said extraction can be performed in the presence of at least one organic solvent that can be selected from: apolar organic solvents such as, for example, iso-octane, n-octane, or mixtures thereof; mixtures of hydrocarbons such as, for example, naphtha or diesel blends that can optionally also derive from the production of green diesel; polar organic solvents such as, for example, methanol, ethanol, iso-propanol, acetone, ethyl acetate, hexane, methyl-tert-butyl ketone, ethyl-tert-butyl ether, or mixtures thereof; or mixtures thereof.

Said extraction can be performed at a temperature ranging from 20° C. to 200° C., preferably at the boiling point of the solvent used.

Said extraction can be performed in the presence of a quantity of solvent ranging from 1 times to 6 times, preferably ranging from 1.5 times to 5 times, the volume of the aqueous phase of the aqueous suspension of exhausted oleaginous cellular biomass comprising lipids obtained from cell lysis.

The aqueous suspension of exhausted oleaginous cellular biomass comprising lipids obtained after said cell lysis can be subjected to extraction one or more times.

Preferably, said aqueous suspension of exhausted oleaginous cellular biomass comprising lipids can be subjected to extraction from 1 times to 5 times, more preferably from 1 time to 3 times.

At the end of the aforementioned extraction, the following two phases are obtained:

(i) an organic phase comprising lipids dissolved in solvent;

(ii) an aqueous phase comprising cellular debris and traces of unseparated lipids.

For the purpose of recovering the lipids, said organic phase (i) is subjected to evaporation, obtaining a high boiling point oil (ia) as residue comprising lipids and a liquid phase containing the solvent that can be recycled to the aforementioned extraction.

Preferably the lipids comprised in said organic phase (i) are triglycerides, more preferably glycerol esters with fatty acids having 14 to 24 carbon atoms, such as palmitic acid, stearic acid, oleic acid, α-linoleic acid, in quantities greater than or equal to 80% by weight, preferably greater than or equal to 90% by weight, with respect to the total weight of the lipids. Other lipids that can be present in said organic phase (i) are: phospholipids, monoglycerides, diglycerides, free fatty acids, or mixtures thereof.

The total quantity of lipids contained in the aqueous suspension of oleaginous cellular biomass obtained after fermentation, like the total quantity of lipids contained in said high boiling point oil (ia), can be determined through methods known in the state of the art such as, for example, the colorimetric method which is based on the reaction of the lipids with phosphoric acid and phospho-vanilline using, for example, the total lipids-sulpho-phospho-vanilline kit sold by Spinreact S.a/S.A.U., Ctra Santa Coloma, 7 E-17176 Sant Esteve de Bas (GI), Spain. Further details on said method can be found, for example, in the following article: "Chemical Basis of the Sulpho-phospho-vanillin Reaction for Estimating Total Serum Lipids", J. A. Knight et al., published in "*Clinical Chemistry*" (1972), Vol. 18, No. 3, pg. 199-202.

Said aqueous phase (ii) comprising the cellular debris, in particular protein and polysaccharides contained in the cell membrane of the oleaginous microorganism used, can be dehumidified and exploited as fuel, optionally associated with the lignin obtained after the hydrolysis of the biomass.

Alternatively, said aqueous phase (ii) can be subjected to anaerobic digestion for producing biogas, which can be used for producing electrical energy, which can also be used for fulfilling the energy requirement of the process according to the present invention.

Alternatively, said aqueous phase (ii) can be subjected to liquefaction for producing bio-oil as described, for example, in international patent applications WO 2010/069583 or WO 2010/069516.

The lipids obtained according to the process of the present invention, can be subjected to esterification in the presence of at least one alcohol having from 1 to 4 carbon atoms, preferably methanol, ethanol, and of at least one acidic or basic catalyst, in order to produce glycerol and alkyl esters, in particular methyl esters or ethyl esters (biodiesel).

Alternatively, said lipids can be subjected to hydrogenation/deoxygenation in the presence of hydrogen and of at least one catalyst in order to produce green diesel.

Hydrogenation/deoxygenation processes are known in the art and are described, for example, in European patent application EP 1,728,844.

The present invention will now be illustrated in more detail through two embodiments with reference to FIG. 1 and FIG. 2 described below.

Figure 1:
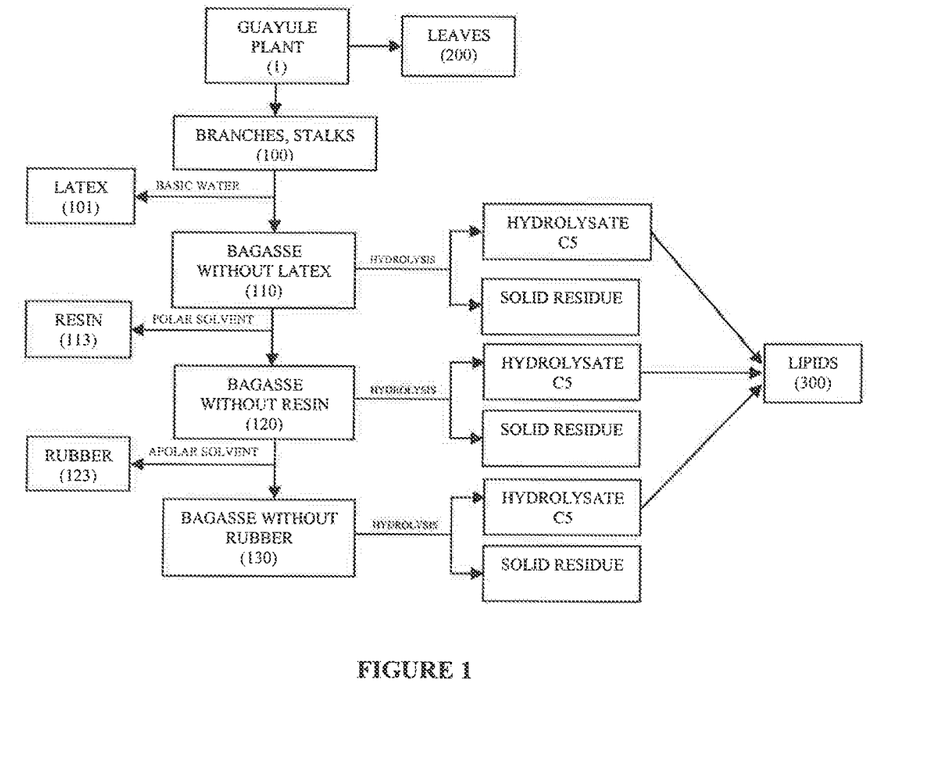

FIG. 1 depicts an embodiment of the process according to the present invention. For that purpose, branches and stalks (100) are separated from the leaves (200) of the guayule plant (1), for example through a mechanical treatment. The leaves (200) can be subjected to further treatments (not shown in FIG. 1), for the purpose of obtaining, for example, waxes and essential oils. The branches and stalks (100) are subjected to extraction in the presence of a basic aqueous solution (indicated as "basic water" in FIG. 1) [for example, a 0.15% by weight basic aqueous solution comprising sodium hydroxide (KOH)] comprising at least one stabilizer (for example an antioxidant) obtaining a first miscella from which is extracted the latex (101) and a first bagasse without latex (110). Said first bagasse without latex (110) is subjected to extraction in the presence of a polar solvent system (indicated as "polar solvent" in FIG. 1) comprising at least one polar organic solvent (for example, ethanol) and at least one stabilizer (for example, an antioxidant) obtaining a second miscella from which the resin (113) is extracted and a second bagasse without latex and without resin [indicated as bagasse without resin (120) in FIG. 1]. Said second bagasse without latex and without resin (120) is subjected to extraction in the presence of an apolar solvent system (indicated as "apolar solvent" in FIG. 1) comprising at least one apolar organic solvent (for example, hexane) and at least one stabilizer (for example, an antioxidant) obtaining a third miscella from which is extracted the rubber (123) and a third bagasse without latex, without resin and without rubber [indicated as bagasse without rubber (130) in FIG. 1].

Subsequently, the three different types of bagasse obtained are subjected to hydrolysis operating according to the various methods described above [for example, to hydrolysis in the presence of an aqueous solution of methanesulfonic acid ($CH_3$—$SO_3H$) at pH 1.1], obtaining a solid residue comprising lignin and cellulose and a hydrolysate comprising 5 carbon atom (C5) sugars. Said solid residue can be subjected to further treatments such as, for example, enzymatic hydrolysis for the purpose of obtaining glucose from the cellulose (not shown in FIG. 1). Said hydrolysate comprising 5 carbon atom (C5) sugars is supplied to a fermentation device in the presence of at least one oleaginous yeast for the purpose of obtaining lipids (300) operating according to the process disclosed by the present invention.

Figure 2:
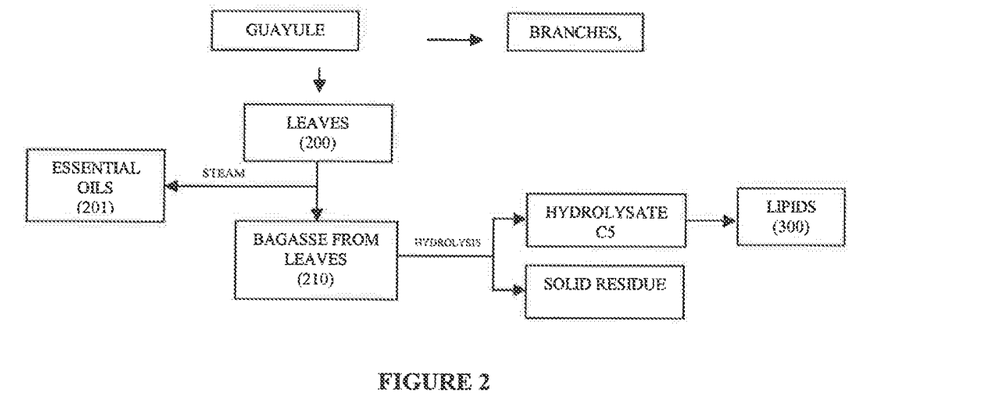

FIG. 2 depicts a further embodiment of the process according to the present invention. For that purpose, branches and stalks (100) are separated from the leaves (200) of the guayule plant (1), for example through a mechanical treatment. The leaves (200) are subjected to extraction in a stream of steam, operating according to methods known in the state of the art as described, for example, by Schmidt E. in "*Handbook of Essential Oil. Science, Technology and Application*" (2010), Baser K. H. C. and Buchbauer G. Eds., CRC Press, Boca Raton (USA), Chapter 4, pg. 99-117, obtaining a mixture of essential oils (201) which is collected separately by cold condensation of the steam and a solid residue, i.e. the bagasse from leaves (210). Said bagasse from leaves (210) is subjected to hydrolysis operating according to the various methods described above [for example, to hydrolysis in the presence of an aqueous solution of methanesulfonic acid ($CH_3$—$SO_3H$) at pH 1.1], obtaining a solid residue comprising lignin and cellulose and a hydrolysate comprising 5 carbon atom (C5) sugars. Said solid residue can be subjected to further treatments such as, for example, enzymatic hydrolysis for the purpose of obtaining glucose from the cellulose (not shown in FIG. 2). Said hydrolysate comprising 5 carbon atom (C5) sugars is fed to a fermentation device in the presence of at least one oleaginous yeast for the purpose of obtaining lipids (300) operating according to the process disclosed by the present invention.

More details on obtaining said various types of bagasse, and for obtaining latex, resin, rubber, essential oils, from guayule plants, can be found, for example, in international patent application WO 2016/062753 in the name of the Applicant reported above, or in Italian patent application IT2015000082659 in the name of the Applicant.

For the purpose of understanding the present invention better and to put it into practice, below are some illustrative and non-limiting examples thereof.

EXAMPLE 1

Fermentation in the Presence of the Hydrolysate Comprising 5 Carbon Atom (C5 (Sugars Obtained from the Hydrolysis of Bagasse without Latex (Conductivity a to 1 mS/cm)

25 g of guayule bagasse (*Parthenium argentatum*) without latex previously ground (particle diameter<2 mm) were loaded into an open top Büchi autoclave type 3E/1.0 lt. Subsequently, 500 g of an aqueous solution of methanesulfonic acid ($CH_3$—$SO_3H$), at pH 1.1, were loaded. The first reaction mixture thus obtained was kept under vigorous stirring (600 rpm), until reaching the temperature of 140° C., over 45 minutes, obtaining a second reaction mixture comprising a solid residue comprising lignin and cellulose and a hydrolysate comprising 5 carbon atom (C5) sugars. After leaving the autoclave to cool down to room temperature (23° C.), said solid residue comprising lignin and cellulose and said hydrolysate comprising 5 carbon atom (C5) sugars were separated by filtration. For the purpose of obtaining the quantity of sugars reported below (i.e. 86.7 g/l), said process was repeated another two times, using 25 g of guayule bagasse (*Parthenium argentatum*) without latex previously ground (particle diameter<2 mm) each time: at the end, the three hydrolysates comprising 5 carbon atom (C5) sugars obtained, were joined in order to have a single hydrolysate.

After having partially removed the methanesulfonic acid ($CH_3$—$SO_3H$) by passing said hydrolysate comprising 5 carbon atom (C5) sugars on an ion exchange column (90 cm×4 cm) DOWEX™ 22 (Dow Chemicals, USA) eluted at a flow rate of 15 ml/min, for 90 minutes, the hydrolysate obtained, after concentration by vacuum evaporation (40 mbar, 40° C.), contained 86.7 g/l of sugars of which: 4.5 g/l glucose, 65.9 g/l xylose, 16.3 g/l arabinose.

The sugar content was determined through ion exchange chromatography (HPAE-PAD), using a Dionex chromatography system, equipped with a Carbopac PA 100 column, with a sodium hydroxide and sodium acetate counter-ion gradient. 173 ml of said hydrolysate, were appropriately diluted with 127 ml of water so as to have a sugar concentration equal to about 50 g/l: the solution obtained was subjected to conductivity measurement at 25° C., using a MM40+ portable conductivity meter made by Crisson Instruments which was equal to 1 mS/cm.

Subsequently, the following were added to said solution, placed in a 500 ml flask, provided with a magnetic stirrer: 1 g/l of yeast extract, 1 g/l of $(NH_4)_2SO_4$, 1 g/l of $KH_2PO_4$, 0.05 g/l of $MgSO_4.7H_2O$, 0.01 g/l di $CaCl_2.2H_2O$, 0.01 g/l of NaCl, and the pH was brought to 6 by adding some drops of 2.5 M potassium hydroxide (KOH). The mixture obtained was sterilized in an autoclave at 121° C., for 20 minutes.

At the end of sterilization, the mixture obtained was brought to room temperature (25° C.) and 30 ml of a 1M stock solution of the buffer MES [2-(N-morpholino)ethanesulfonic acid] were added in order to obtain a pH of 6 and split into three 500 ml flasks. Each of said flasks was inoculated with a cell suspension (inoculum) having a concentration of 0.1 $OD_{660}$/ml of:

*Rhodosporidium azoricum* DSM 29495 (flask 1);
*Trichosporon pullulans* NRRL Y-1522 (flask 2);
*Trichosporon oleaginous* ATCC 20509 (flask 3).

The aforementioned cell suspension (inoculum) was obtained by cultivating cells of three different strains, in three different 500 ml flasks, in 100 ml of "YEPD" medium (yeast extract 10 g/l, peptone 10 g/l, glucose 20 g/l): the flasks were placed in an agitated incubator (200 rpm), at 30° C., for one night.

The cell growth during fermentation was measured with a spectrophotometer determining the turbidity, or optical density (OD) of a sample of fermentation broth at 660 nm ($OD_{660}$).

The flasks thus inoculated, were left to grow, for 120 hours, at 30° C., under stirring (200 rpm).

For comparative purposes, another three flasks were inoculated containing a synthetic culture medium including 50 g/l of xylose, 1 g/l of yeast extract, 1 g/l of $(NH_4)_2SO_4$, 1 g/l of $KH_2PO_4$, 0.05 g/l of $MgSO_4.7H_2O$, 0.01 g/l of $CaCl_2.2H_2O$, 0.01 g/l of NaCl and 30 ml of a 1 M stock solution of the buffer MES [2-(N-morpholino)ethanesulfonic acid] so as to have a pH of 6, with the cell suspensions (inocula) reported above (flask 1a), (flask 2a) and (flask 3a), respectively.

At the end of fermentation, a sample of fermentation broth (5 ml) was taken from each flask, which was subjected to centrifugation for 10 minutes, at 4000 rpm, obtaining an aqueous suspension of concentrated oleaginous cellular biomass comprising lipids and an aqueous phase. Said aqueous suspension of concentrated oleaginous cellular biomass comprising lipids was used for determining the dry weight (through filtration and subsequent heat treatment) and the lipids (using the total lipids-sulpho-phospho vanilline kit) operating as described above, and obtaining the following values:

strain of oleaginous yeast of the species *Rhodosporidium azoricum* DSM 29495 (flask 1a) had reached a cell concentration of 11.1 g/l (or, quantity of biomass expressed as dry weight of cells in g per liter of medium), containing 38% by weight of lipids (or, quantity of accumulated lipids expressed as a percentage ratio between weight of lipids and total dry weight);

strain of oleaginous yeast of the species *Rhodosporidium azoricum* DSM 29495 (flask 1) had reached a cell concentration of 12.9 g/l (or, quantity of biomass expressed as dry weight of cells in g per liter of medium), containing 33% by weight of lipids (or, quantity of accumulated lipids expressed as a percentage ratio between weight of lipids and total dry weight);

strain of oleaginous yeast of the species *Trichosporon pullulans* NRRL Y-1522 (flask 2a) had reached a cell concentration of 16.4 g/l (or, quantity of biomass expressed as dry weight of cells in g per liter of medium), containing 43% by weight of lipids (or, quantity of accumulated lipids expressed as a percentage ratio between weight of lipids and total dry weight);

strain of oleaginous yeast of the species *Trichosporon pullulans* NRRL Y-1522 (flask 2) had reached a cell concentration of 16.3 g/l (or, quantity of biomass expressed as dry weight of cells in g per liter of medium), containing 39% by weight of lipids (or, quantity of accumulated lipids expressed as a percentage ratio between weight of lipids and total dry weight);

strain of oleaginous yeast of the species *Trichosporon oleaginous* ATCC 20509 (flask 3a) had reached a cell concentration of 15.1 g/l (or, quantity of biomass expressed as dry weight of cells in g per liter of medium), containing 38% by weight of lipids (or, quantity of accumulated lipids expressed as a percentage ratio between weight of lipids and total dry weight);

strain of oleaginous yeast of the species *Trichosporon oleaginous* ATCC 20509 (flask 3) had reached a cell concentration of 17.6 g/l (or, quantity of biomass expressed as dry weight of cells in g per liter of medium), containing 38% by weight of lipids (or, quantity of accumulated lipids expressed as a percentage ratio between weight of lipids and total dry weight).

From the data reported above, it can be deduced that the use of the hydrolysate from bagasse without latex allows both the growth of the cell biomass, and the production of lipids, of the three strains analyzed.

EXAMPLE 2

Fermentation in the presence of the hydrolysate comprising 5 carbon atom (C5) sugars obtained from the hydrolysis of bagasse without latex (conductivity equal to 10 mS/cm)

25 g of guayule bagasse (*Parthenium argentatum*) without latex previously ground (particle diameter<2 mm) were loaded into an open top Bichi autoclave type 3E/1.0 lt. Subsequently, 500 g of an aqueous solution of methanesulfonic acid ($CH_3$—$SO_3H$), at pH 1.1, were loaded. The first reaction mixture thus obtained was kept under vigorous stirring (600 rpm), until reaching the temperature of 140° C., over 45 minutes, obtaining a second reaction mixture comprising a solid residue comprising lignin and cellulose and a hydrolysate comprising 5 carbon atom (C5) sugars. After leaving the autoclave to cool down to room temperature (23° C.), said solid residue comprising lignin and cellulose and said hydrolysate comprising 5 carbon atom (C5) sugars were separated by filtration. For the purpose of obtaining the quantity of sugars reported below (i.e. 55 g/), said process was repeated another two times, using 25 g of guayule bagasse (*Parthenium argentatum*) without latex previously ground (particle diameter<2 mm) each time: at the end, the three hydrolysates comprising 5 carbon atom (C5) sugars obtained, were joined in order to have a single hydrolysate.

Said hydrolysate comprising 5 carbon atom (C5) sugars, after concentration by vacuum evaporation (40 mbar, 40° C.), contained 55 g/l of sugars of which: 3.7 g/l glucose, 39.3 g/l xylose, 10.4 g/l arabinose, 1.6 g cellobiose.

The sugars were determined as described in Example 1.

269.7 ml of said hydrolysate, were appropriately diluted with 30.3 ml of water so as to have a sugar concentration equal to about 50 g/l: the solution obtained was subjected to conductivity measurement at 25° C., using a MM40+ portable conductivity meter made by Crisson Instruments which was equal to 10 mS/cm.

Subsequently, the following were added to said solution, placed in a 500 ml flask, provided with a magnetic stirrer: 1 g/l of yeast extract, 1 g/l of $(NH_4)_2SO_4$, 1 g/l of $KH_2PO_4$, 0.05 g/l of $MgSO_4.7H_2O$, 0.01 g/l di $CaC_2.2H_2O$, 0.01 g/l of NaCl, and the pH of the same was brought to 6 by adding some drops of 2.5 M potassium hydroxide (KOH). The mixture obtained was sterilized in an autoclave at 121° C., for 20 minutes.

At the end of sterilization, the mixture obtained was brought to room temperature (25° C.) and 30 ml of a 1M stock solution of the buffer MES [2-(N-morpholino)ethanesulfonic acid] were added in order to obtain a pH of 6 and split into three 500 ml flasks. Each of said flasks was inoculated with a cell suspension (inoculum) having a concentration of 0.1 $OD_{000}$/ml of:

*Rhodosporidium azoricum* DSM 29495 (flask 4);
*Trichosporon pullulans* NRRL Y-1522 (flask 5);
*Trichosporon oleaginous* ATCC 20509 (flask 6).

The flasks thus inoculated, were left to grow, for 24 hours, at 30° C., under stirring (200 rpm).

The aforementioned cell suspension (inoculum) was obtained as described in Example 1.

For comparative purposes, the cultures in synthetic medium of Example 1 were used: the comparison values are, therefore, those reported in Example 1 for (flask 1a), (flask 2a) and (flask 3a).

The cell growth during fermentation was measured with a spectrophotometer determining the turbidity, or optical density (OD) of a sample of fermentation broth at 660 nm ($OD_{660}$).

At the end of fermentation, a sample of fermentation broth (5 ml) was taken from each flask and the following values were determined, operating as described in Example 1:

strain of oleaginous yeast of the species *Rhodosporidium azoricum* DSM 29495 (flask 4) had reached a cell concentration of 17.5 g/l (or, quantity of biomass expressed as dry weight of cells in g per liter of medium), containing 8% by weight of lipids (or, quantity of accumulated lipids expressed as a percentage ratio between weight of lipids and total dry weight) [comparison with (flask 1a)];

strain of oleaginous yeast of the species *Trichosporon pullulans* NRRL Y-1522 (flask 5) had reached a cell concentration of 22.0 g/l (or, quantity of biomass expressed as dry weight of cells in g per liter of medium), containing 21% by weight of lipids (or, quantity of accumulated lipids expressed as a percentage ratio between weight of lipids and total dry weight) [comparison with (flask 2a)];

strain of oleaginous yeast of the species *Trichosporon oleaginous* ATCC 20509 (flask 6) had reached a cell concentration of 21.3 g/l (or, quantity of biomass expressed as dry weight of cells in g per liter of medium), containing 24% by weight of lipids (or, quantity of accumulated lipids expressed as a percentage ratio between weight of lipids and total dry weight) [comparison with (flask 3a)].

From the data reported above, it can be deduced that the use of the hydrolysate from bagasse without latex with high conductivity allows both the growth of the cell biomass, and the production of lipids, of the three strains analyzed despite the high level of salts (i.e. conductivity equal to 10 mS/cm).

EXAMPLE 3

Fermentation in the Presence of the Hydrolysate Comprising 5 Carbon Atom (C5) Sugars Obtained from the Hydrolysis of Bagasse without Latex and without Resin (Conductivity Equal to 0.15 mS/cm)

25 g of guayule bagasse (*Parthenium argentatum*) without latex and without resin previously ground (particle diameter<2 mm) were loaded into an open top Büchi autoclave type 3E/1.0 lt.

Subsequently, 500 g of an aqueous solution of methanesulfonic acid ($CH_3$—$SO_3H$), at pH 1.1, were loaded. The first reaction mixture thus obtained was kept under vigorous stirring (600 rpm), until reaching the temperature of 140° C., over 45 minutes, obtaining a second reaction mixture comprising a solid residue comprising lignin and cellulose and a hydrolysate comprising 5 carbon atom (C5) sugars. After leaving the autoclave to cool down to room temperature (23° C.), said solid residue comprising lignin and cellulose and said hydrolysate comprising 5 carbon atom (C5) sugars were separated by filtration. For the purpose of obtaining the quantity of sugars reported below (i.e. 46.7 g/l), said process was repeated another two times, using 25 g of guayule bagasse (*Parthenium argentatum*) without latex and without resin previously ground (particle diameter<2 mm) each time: at the end the three hydrolysates comprising 5 carbon atom (C5) sugars obtained, were joined in order to have a single hydrolysate.

After having partially removed the methanesulfonic acid ($CH_3$—$SO_3H$) by passing said hydrolysate comprising 5 carbon atom (C5) sugars on an ion exchange column (90 cm×4 cm) DOWEX™ 22 (Dow Chemicals, USA) eluted at a flow rate of 15 ml/min, for 90 minutes, the hydrolysate obtained, after concentration by vacuum evaporation (40 mbar, 40° C.), contained 46.7 g/l of sugars of which: 3.3 g/l glucose, 29.2 g/l xylose, 13.9 g/l arabinose, 0.3 g cellobiose: said hydrolysate was subjected to conductivity measurement at 25° C., using a MM40+ portable conductivity meter made by Crisson Instruments which was equal to 0.15 mS/cm.

The sugars were determined as described in Example 1.

300 ml of said hydrolysate, having an initial sugar concentration of 46.7 g/l, were placed in a 500 ml flask, equipped with a magnetic stirrer, to which the following were subsequently added: 1 g/l of yeast extract, 1 g/l of $(NH_4)_2SO_4$, 1 g/l of $KH_2PO_4$, 0.05 g/l of $MgSO_4.7H_2O$, 0.01 g/l di $CaCl_2.2H_2O$, 0.01 g/l of NaCl, and the pH of the same was brought to 6 by adding some drops of 2.5 M potassium hydroxide (KOH). The mixture obtained was sterilized in an autoclave at 121° C., for 20 minutes.

At the end of sterilization, the mixture obtained was brought to room temperature (25° C.) and 30 ml of a 1M stock solution of the buffer MES [2-(N-morpholino)ethanesulfonic acid] were added in order to obtain a pH of 6 and split into three 500 ml flasks. Each of said flasks was inoculated with a cell suspension (inoculum) having a concentration of 0.1 $OD_{660}$/ml of:

*Rhodospordium azoricum* DSM 29495 (flask 7);
*Trichosporon pullulans* NRRL Y-1522 (flask 8);
*Trichosporon oleaginous* ATCC 20509 (flask 9).

The flasks thus inoculated, were left to grow, for 24 hours, at 30° C., under stirring (200 rpm).

The aforementioned cell suspension (inoculum) was obtained as described in Example 1.

For comparative purposes, the cultures in synthetic medium of Example 1 were used: the comparison values are, therefore, those reported in Example 1 for (flask 1a), (flask 2a) and (flask 3a).

The cell growth during fermentation was measured with a spectrophotometer determining the turbidity, or optical density (OD) of a sample of fermentation broth at 660 nm ($OD_{660}$).

At the end of fermentation, a sample of fermentation broth (5 ml) was taken from each flask and the following values were determined, operating as described in Example 1:

strain of oleaginous yeast of the species *Rhodosporidium azoricum* DSM 29495 (flask 7) had reached a cell concentration of 14.8 g/l (or, quantity of biomass expressed as dry weight of cells in g per liter of medium), containing 66% by weight of lipids (or, quantity of accumulated lipids expressed as a percentage ratio between weight of lipids and total dry weight) [comparison with (flask 1a)];

strain of oleaginous yeast of the species *Trichosporon pullulans* NRRL Y-1522 (flask 8) had reached a cell concentration of 21.4 g/l (or, quantity of biomass expressed as dry weight of cells in g per liter of medium), containing 35% by weight of lipids (or, quantity of accumulated lipids expressed as a percentage ratio between weight of lipids and total dry weight) [comparison with (flask 2a)];

strain of oleaginous yeast of the species *Trichosporon oleaginous* ATCC 20509 (flask 9) had reached a cell concentration of 18.4 g/l (or, quantity of biomass expressed as dry weight of cells in g per liter of medium), containing 37% by weight of lipids (or, quantity of accumulated lipids expressed as a percentage ratio between weight of lipids and total dry weight) [comparison with (flask 3a)].

From the data reported above, it can be deduced that the use of the hydrolysate from bagasse without latex and without resin allows both the growth of the cell biomass, and the production of lipids, of the three strains analyzed.

EXAMPLE 4

Fermentation in the Presence of the Hydrolysate Comprising 5 Carbon Atom (C5) Sugars Obtained from the Hydrolysis of Bagasse without Latex, without Resin and without Rubber (Conductivity Equal to 0.18 mS/cm)

25 g of guayule bagasse (*Parthenium argentatum*) without latex, without resin and without rubber previously ground (particle diameter<2 mm) were loaded into an open top Büchi autoclave type 3E/1.0 lt.

Subsequently, 500 g of an aqueous solution of methanesulfonic acid ($CH_3$—$SO_3H$), at pH 1.1, were loaded. The first reaction mixture thus obtained was kept under vigorous stirring (600 rpm), until reaching the temperature of 140° C., over 45 minutes, obtaining a second reaction mixture comprising a solid residue comprising lignin and cellulose and a hydrolysate comprising 5 carbon atom (O5) sugars. After leaving the autoclave to cool down to room temperature (23°

C.), said solid residue comprising lignin and cellulose and said hydrolysate comprising 5 carbon atom (C5) sugars were separated by filtration. For the purpose of obtaining the quantity of sugars reported below (i.e. 52 g/l), said process was repeated another two times, using 25 g of guayule bagasse (*Parthenium argentatum*) without latex, without resin and without rubber previously ground (particle diameter<2 mm) each time: at the end, the three hydrolysates comprising 5 carbon atom (C5) sugars obtained, were joined in order to have a single hydrolysate.

After having partially removed the methanesulfonic acid ($CH_3$—$SO_3H$) by passing said hydrolysate comprising 5 carbon atom (C5) sugars on an ion exchange column (90 cm×4 cm) DOWEX™ 22 (Dow Chemicals, USA) eluted at a flow rate of 15 ml/min, for 90 minutes, the hydrolysate obtained, after concentration by vacuum evaporation (40 mbar, 40° C.), contained 52 g/l of sugars of which: 2.3 g/l glucose, 34.8 g/l xylose, 14.5 g/l arabinose, 0.4 g cellobiose: said hydrolysate was subjected to conductivity measurement at 25° C., using a MM40+ portable conductivity meter made by Crisson Instruments which was equal to 0.18 mS/cm.

The sugars were determined as described in Example 1.

300 ml of said hydrolysate, having an initial sugar concentration of 52 g/l, were placed in a 500 ml flask, equipped with a magnetic stirrer, to which the following were subsequently added: 1 g/l of yeast extract, 1 g/l of $(NH_4)_2SO_4$, 1 g/l of $KH_2PO_4$, 0.05 g/of $MgSO_4.7H_2O$, 0.01 g/l di $CaCl_2.2H_2O$, 0.01 g/l of NaCl, and the pH was brought to 6 by adding some drops of 2.5 M potassium hydroxide (KOH). The mixture obtained was sterilized in an autoclave at 121° C., for 20 minutes.

At the end of sterilization, the mixture obtained was brought to room temperature (25° C.) and 30 ml of a 1M stock solution of the buffer MES [2-(N-morpholino)ethanesulfonic acid] were added in order to obtain a pH of 6 and split into three 500 ml flasks. Each of said flasks was inoculated with a cell suspension (inoculum) having a concentration of 0.1 $OD_{660}$/ml of:

*Rhodosporidium azoricum* DSM 29495 (flask 10);
*Trichosporon pullulans* NRRL Y-1522 (flask 11);
*Trichosporon oleaginous* ATCC 20509 (flask 12).

The flasks thus inoculated, were left to grow, for 120 hours, at 30° C., under stirring (200 rpm).

The aforementioned cell suspension (inoculum) was obtained as described in Example 1.

For comparative purposes, the cultures in synthetic medium of Example 1 were used: the comparison values are, therefore, those reported in Example 1 for (flask 1a), (flask 2a) and (flask 3a).

The cell growth during fermentation was measured with a spectrophotometer determining the turbidity, or optical density (OD) of a sample of fermentation broth at 660 nm ($OD_{660}$).

At the end of fermentation, a sample of fermentation broth (5 ml) was taken from each flask and the following values were determined, operating as described in Example 1:

strain of oleaginous yeast of the species *Rhodosporidium azoricum* DSM 29495 (flask 10) had reached a cell concentration of 16 g/l (or, quantity of biomass expressed as dry weight of cells in g per liter of medium), containing 65% by weight of lipids (or, quantity of accumulated lipids expressed as a percentage ratio between weight of lipids and total dry weight) [comparison with (flask 1a)];

strain of oleaginous yeast of the species *Trichosporon pullulans* NRRL Y-1522 (flask 11) had reached a cell concentration of 20.8 g/l (or, quantity of biomass expressed as dry weight of cells in g per liter of medium), containing 40% by weight of lipids (or, quantity of accumulated lipids expressed as a percentage ratio between weight of lipids and total dry weight) [comparison with (flask 2a)];

strain of oleaginous yeast of the species *Trichosporon oleaginous* ATCC 20509 (flask 12) had reached a cell concentration of 18 g/l (or, quantity of biomass expressed as dry weight of cells in g per liter of medium), containing 45% by weight of lipids (or, quantity of accumulated lipids expressed as a percentage ratio between weight of lipids and total dry weight) [comparison with (flask 3a)].

From the data reported above, it can be deduced that the use of the hydrolysate from bagasse without latex, without resin and without rubber allows both the growth of the cell biomass, and the production of lipids, of the three strains analyzed.

EXAMPLE 5

Fermentation in the Presence of the Hydrolysate Comprising 5 Carbon Atom (C5) Sugars Obtained from the Hydrolysis of Bagasse from Leaves (Conductivity Equal to 0.20 mS/cm)

25 g of bagasse from guayule leaves (*Parthenium argentatum*) previously ground (particle diameter<2 mm) were loaded into an open top Büchi autoclave type 3E/1.0 lt. Subsequently, 500 g of an aqueous solution of methanesulfonic acid ($CH_3$—$SO_3H$), at pH 1.1, were loaded. The first reaction mixture thus obtained was kept under vigorous stirring (600 rpm), until reaching the temperature of 140° C., over 45 minutes, obtaining a second reaction mixture comprising a solid residue comprising lignin and cellulose and a hydrolysate comprising 5 carbon atom (C5) sugars. After leaving the autoclave to cool down to room temperature (23° C.), said solid residue comprising lignin and cellulose and said hydrolysate comprising 5 carbon atom (C5) sugars were separated by filtration. For the purpose of obtaining the quantity of sugars reported below (i.e. 51.3 g/l), said process was repeated another two times, using 25 g of bagasse from guayule leaves (*Parthenium argentatum*) previously ground (particle diameter<2 mm) each time: at the end the three hydrolysates comprising 5 carbon atom (C5) sugars obtained, were joined in order to have a single hydrolysate.

After having partially removed the methanesulfonic acid ($CH_3$—$SO_3H$) by passing said hydrolysate comprising 5 carbon atom (C5) sugars on an ion exchange column (90 cm×4 cm) DOWEX™ 22 (Dow Chemicals, USA) eluted at a flow rate of 15 ml/min, for 90 minutes, the hydrolysate obtained, after concentration by vacuum evaporation (40 mbar, 40° C.), contained 51.3 g/l of sugars of which: 8.4 g/l glucose, 27.6 g/l xylose, 15.3 g/l arabinose: said hydrolysate was subjected to conductivity measurement at 25° C., using a MM40+ portable conductivity meter made by Crisson Instruments which was equal to 0.18 mS/cm.

The sugars were determined as described in Example 1.

300 ml of said hydrolysate, having an initial sugar concentration of 51.33 g/l, were placed in a 500 ml flask, equipped with a magnetic stirrer, to which the following were subsequently added: 1 g/l of yeast extract, 1 g/l of $(NH_4)_2SO_4$, 1 g/l of $KH_2PO_4$, 0.05 g/of $MgSO_4.7H_2O$, 0.01 g/l di $CaCl_2.2H_2O$, 0.01 g/l of NaCl, and the pH was brought to 6 by adding some drops of 2.5 M potassium hydroxide (KOH). The mixture obtained was sterilized in an autoclave at 121° C., for 20 minutes.

At the end of sterilization, the mixture obtained was brought to room temperature (25° C.) and 30 ml of a 1M stock solution of the buffer MES [2-(N-morpholino)ethane-sulfonic acid] were added in order to obtain a pH of 6 and split into three 500 ml flasks. Each of said flasks was inoculated with a cell suspension (inoculum) having a concentration of 0.1 $OD_{660}$/ml of:

Rhodosporidium azoricum DSM 29495 (flask 13);
Trichosporon pullulans NRRL Y-1522 (flask 14);
Trichosporon oleaginous ATCC 20509 (flask 15).

The flasks thus inoculated, were left to grow, for 24 hours, at 30° C., under stirring (200 rpm).

The aforementioned cell suspension (inoculum) was obtained as described in Example 1.

For comparative purposes, the cultures in synthetic medium of Example 1 were used: the comparison values are, therefore, those reported in Example 1 for (flask 1a), (flask 2a) and (flask 3a).

The cell growth during fermentation was measured with a spectrophotometer determining the turbidity, or optical density (OD) of a sample of fermentation broth at 660 nm ($OD_{660}$).

At the end of fermentation, a sample of fermentation broth (5 ml) was taken from each flask and the following values were determined, operating as described in Example 1:

- strain of oleaginous yeast of the species Rhodosporidium azoricum DSM 29495 (flask 13) had reached a cell concentration of 10 g/l (or, quantity of biomass expressed as dry weight of cells in g per liter of medium), containing 30% by weight of lipids (or, quantity of accumulated lipids expressed as a percentage ratio between weight of lipids and total dry weight) [comparison with (flask 1a)];
- strain of oleaginous yeast of the species Trichosporon pullulans NRRL Y-1.522 (flask 14) had reached a cell concentration of 15 g/l (or, quantity of biomass expressed as dry weight of cells in g per liter of medium), containing 21% by weight of lipids (or, quantity of accumulated lipids expressed as a percentage ratio between weight of lipids and total dry weight) [comparison with (flask 2a)];
- strain of oleaginous yeast of the species Trichosporon oleaginous ATCC 20509 (flask 15) had reached a cell concentration of 14.5 g/l (or, quantity of biomass expressed as dry weight of cells in g per liter of medium), containing 25% by weight of lipids (or, quantity of accumulated lipids expressed as a percentage ratio between weight of lipids and total dry weight) [comparison with (flask 3a)].

From the data reported above, it can be deduced that the use of the hydrolysate from bagasse from leaves allows both the growth of the cell biomass, and the production of lipids, of the three strains analyzed.

The following Tables 1, 2 and 3, show the data obtained as reported in Examples 1-5 in terms of cell concentration (i.e. quantity of biomass expressed as dry weight in g per liter of culture) and lipids (i.e. quantity of accumulated lipids expressed as percentage ratio between weight of lipids and total dry weight).

TABLE 1

| Rhodosporidium azoricum DSM 29495 | | |
|---|---|---|
| EXAMPLE | DRY WEIGHT (g/l) | LIPIDS (%) |
| Control (flask 1a) | 11.1 | 38 |
| 1 (flask 1) | 12.9 | 33 |
| 2 (flask 4) | 17.5 | 8 |
| 3 (flask 7) | 14.8 | 66 |
| 4 (flask 10) | 16 | 65 |
| 5 (flask 13) | 10 | 30 |

TABLE 2

| Trichosporon pullulans NRRL Y-522 | | |
|---|---|---|
| EXAMPLE | DRY WEIGHT (g/l) | LIPIDS (%) |
| Control (flask 2a) | 16.4 | 43 |
| 1 (flask 2) | 16.3 | 39 |
| 2 (flask 5) | 22 | 21 |
| 3 (flask 8) | 21.4 | 35 |
| 4 (flask 11) | 20.8 | 40 |
| 5 (flask 14) | 15 | 21 |

TABLE 3

| Trichosporon oleaginous ATCC 20509 | | |
|---|---|---|
| EXAMPLE | DRY WEIGHT (g/l) | LIPIDS (%) |
| Control (flask 3a) | 15.1 | 38 |
| 1 (flask 3) | 17.6 | 38 |
| 2 (flask 6) | 21.3 | 24 |
| 3 (flask 9) | 18.4 | 37 |
| 4 (flask 12) | 18 | 45 |
| 5 (flask 15) | 14.5 | 25 |

The invention claimed is:

1. A process for the production of lipids from biomass derived from guayule plants comprising:
    obtaining a hydrolysate comprising 5 carbon atom (C5) sugars from biomass derived from guayule plants, said 5 carbon atom (C5) sugars being present in said hydrolysate in a quantity greater than or equal to 80% by weight, with respect to the total weight of said hydrolysate;
    feeding said hydrolysate to a fermentation device in the presence of at least one oleaginous yeast to obtain a fermentation broth;
    conducting fermentation of said fermentation broth;
    at the end of said fermentation, subjecting said fermentation broth to separation obtaining an aqueous suspension of oleaginous cellular biomass comprising lipids and an aqueous phase.

2. A process for the production of lipids from biomass derived from guayule plants according to claim 1, wherein said hydrolysate is derived from hydrolysis of hemicellulose contained in the guayule plants.

3. A process for the production of lipids from biomass derived from guayule plants according to claim 1, wherein said hydrolysate is derived from hydrolysis of hemicellulose contained in bagasse resulting from extraction processes to which said guayule plants are subjected.

4. Process for the production of lipids from biomass derived from guayule plants according to claim 1, wherein said fermentation is performed:

at a temperature ranging from 20° C. to 40° C.; and/or
for a time ranging from 70 hours to 140 hours; and/or
at a pH ranging from 4.5 to 7.

5. Process for the production of lipids from biomass derived from guayule plants according to claim 1, wherein said oleaginous yeast is selected from: *Rhodosporidium azoricum, Trichosporon pullulans, Trichosporon oleaginous, Trichosporon cacaoliposimilis, Cryptococcus curvatus, Rhodotorula gracili, Rhodotorula graminis, Lypomices starkeyi, Lypomices lipofer, Trigonopsis variabilis, Candida kefyr, Candida curved, Candida lipolytica, Torulopsis* sp., or *Pichia stipitis*.

6. Process for the production of lipids from biomass derived from guayule plants according to claim 1, wherein said fermentation is a batch fermentation, a fed-batch fermentation or a continuous culture fermentation.

7. Process for the production of lipids from biomass derived from guayule plants according to claim 1 wherein said 5 carbon atom (C5) sugars are present in said hydrolysate in a quantity ranging from 85% by weight to 99% by weight, with respect to the total weight of said hydrolysate.

* * * * *